United States Patent [19]

Schmidhammer et al.

[11] Patent Number: 4,482,770
[45] Date of Patent: Nov. 13, 1984

[54] REMOVAL OF ACETYLENE FROM PRODUCTS OF 1,2-DICHLOROETHANE PYROLYSIS

[75] Inventors: Ludwig Schmidhammer, Haiming/Marktl; Rudolf Strasser, Burghausen, both of Fed. Rep. of Germany

[73] Assignee: Wacker Chemie GmbH, Munich, Fed. Rep. of Germany

[21] Appl. No.: 241,281

[22] Filed: Mar. 6, 1981

[51] Int. Cl.³ .............................................. C07C 17/38
[52] U.S. Cl. .................................. 570/219; 570/221; 570/239; 423/488
[58] Field of Search ...................... 570/219, 221, 239; 423/488

[56] References Cited

U.S. PATENT DOCUMENTS 3,466,338 9/1969 Kaneko et al. ................. 260/656
3,987,119 10/1976 Kurtz et al. ..................... 570/219

FOREIGN PATENT DOCUMENTS

| | | | |
|---|---|---|---|
| 887042 | 8/1953 | Fed. Rep. of Germany | 570/227 |
| 1100616 | 9/1961 | Fed. Rep. of Germany | 570/226 |
| 1568679 | 3/1970 | Fed. Rep. of Germany | 570/219 |
| 2353437 | 5/1975 | Fed. Rep. of Germany | 570/243 |
| 731844 | 6/1955 | United Kingdom | 570/226 |
| 1405714 | 9/1975 | United Kingdom | 423/488 |

Primary Examiner—Charles F. Warren
Assistant Examiner—Joseph A. Boska
Attorney, Agent, or Firm—Joel G. Ackerman

[57] ABSTRACT

An improved process for the removal of acetylene from a hydrogen chloride stream in which the acetylene is converted to vinyl chloride by contact with a hydrochlorination catalyst, the improvement comprising, prior to contacting the stream with the hydrochlorination catalyst, contacting said stream with a catalyst comprising a noble metal, preferably of the platinum group, or salt or oxide thereof, supported or unsupported, at a temperature of between about 50° and about 200° C. and a pressure between about 8 and about 20 bar absolute.

7 Claims, 1 Drawing Figure

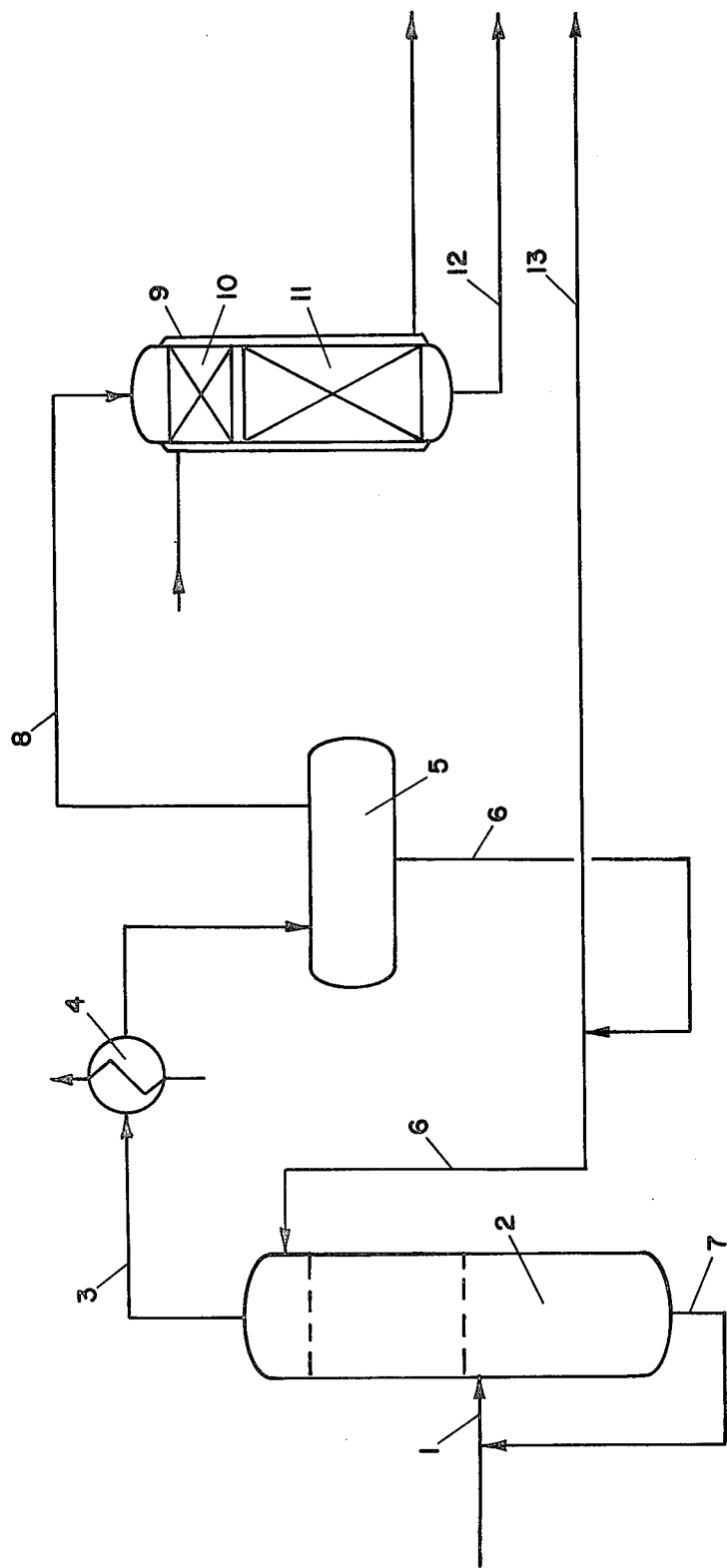

REMOVAL OF ACETYLENE FROM PRODUCTS OF 1,2-DICHLOROETHANE PYROLYSIS

This invention relates to a process for the removal of acetylene from the reaction products of thermal cracking or pyrolysis of 1,2-dichloroethane.

Modern technology for large scale production of vinyl chloride from ethylene employs a cyclical process involving one or more steps. In such a process, typically, ethylene is converted to 1,2-dichloroethane by direct chlorination (usually with chlorine) and/or oxychlorination (using air, oxygen, or oxygen-enriched air, together with hydrogen chloride). The dichloroethane is cracked or pyrolyzed to produce vinyl chloride and hydrogen chloride. The pyrolysis products are cooled, and vinyl chloride, hydrogen chloride, and unreacted dichloroethane are separated. The hydrogen chloride is generally recycled as feed to the oxychlorination step.

During the pyrolysis of 1,2-dichloroethane, small amounts of acetylene are formed as a by-product. The acetylene is generally carried along with the hydrogen chloride, to the oxychlorination unit. However, under oxychlorination conditions, acetylene forms by-products, particularly chloroethylenes, which may interfere with the pyrolysis of dichloroethane and/or the polymerization of vinyl chloride. Hence, the acetylene must be removed from the hydrogen chloride stream before the latter is introduced into the oxychlorination step.

It has heretofore been proposed that the acetylene be removed by a number of methods including the following:

German Auslegeschrift No. 1,568,679 recommends that acetylene contained in the hydrogen chloride be hydrogenated with excess hydrogen in the presence of catalysts comprised of or containing platinum or palladium or their oxides. German Patent application No. 2,353,437 suggests a further development of such a hydrogenation process by providing the catalyst bed with an increasing activity profile of the catalyst in the direction of flow of materials. The hydrogenation converts the acetylene to ethylene, which is suitable as a feed for an oxychlorination process.

However, such hydrogenation processes decrease the carbon yields of the process, since in any process designed for complete conversion, ethane is formed in addition to ethylene. The ethane, however, is lost as an inert gas. Additionally, it is necessary to use relatively large amounts of catalyst if the rate of gas flow is to be maintained, which is necessary for a satisfactory space/time yield.

Other processes are known in which acetylene is removed by hydrochlorination. As described in U.S. Pat. Nos. 2,412,308 and 2,474,206, German Patent No. 887,042, and British Patent No. 721,844, for instance, in such processes the pyrolysis of 1,2-dichloroethane to vinyl chloride is combined with the hydrochlorination of acetylene with hydrogen chloride and the acetylene resulting from the pyrolysis process is converted to vinyl chloride, together with additional acetylene supplied from an external source. Because of the present high price of acetylene, such methods are not currently economical.

British Patent No. 1,405,714 describes the use of a copper or mercury compound supported on active charcoal for removal of small amounts of acetylene from a hydrogen chloride stream. U.S. Pat. No. 4,065,513 states that this removal can be accomplished by the use of activated carbon alone, without a hydrochlorination catalyst, at temperatures of at least 375° F. (190.6° C.).

Furthermore, processes for the manufacture of acetylene-free vinyl chloride have been proposed in which the acetylene is removed from the products of 1,2-dichloroethane pyrolysis by condensing out the uncracked dichloroethane, passing the remaining vinyl chloride-hydrogen chloride mixture over a mercuric chloride-activated carbon catalyst and washing out the hydrogen chloride with water (cf. Belgian Patent No. 564,178).

According to German Patent No. 1,100,616, this process can be varied by condensing most of the hydrogen chloride before the unreacted 1,2-dichloroethane is condensed, by injecting steam into the pyrolysis zone.

However, in these processes the hydrogen chloride is obtained as an aqueous solution of hydrochloric acid rather than as a gas, and is not readily recycleable to the oxychlorination unit.

It is also generally known that all the previously described processes fail to adequately solve the problem which lies in the short life span of the catalyst used for the removal of acetylene, especially when high system pressures are used, as is necessary for an economical space/time yield of the equipment, since at elevated pressures the hydrogenation catalysts are highly subject to sooting. Not only does soot reduce the catalyst activity, it also favors a decomposition reaction of acetylene into additional soot. Furthermore, the effectiveness of the generally known hydrochlorination catalysts decreases relatively rapidly in the presence of low acetylene content, as they are especially sensitive to catalyst poisons and as their activity is oriented more towards a continuous load than towards complete conversion. The performance of activated carbon may be adversely affected by polymerization and/or decomposition of vinyl chloride and/or 1,2-dichloroethane contained in the gaseous stream.

The problem to be solved by this invention consists of making available a catalyst system for the removal of acetylene by the hydrochlorination of acetylene to vinyl chloride, which at system pressures of 8 to 20 bar would result in improved catalyst life.

SUMMARY OF THE INVENTION

This invention comprises a process for the removal of acetylene from the products of thermal pyrolysis of 1,2-dichloroethane in which the pyrolysis products are separated into liquid and gaseous products, and the gaseous product is contacted with a hydrochlorination catalyst whereby the acetylene is converted to vinyl chloride, in which the process is improved by contacting the gaseous stream, prior to contacting it with the hydrochlorination catalyst, with a noble metal or compound thereof, at a temperature of from about 50° to about 200° C., and a pressure of from about 8 to about 20 bar absolute.

DESCRIPTION OF THE DRAWING

The drawing represents a block flow diagram illustrating the process.

DETAILED DESCRIPTION OF THE INVENTION

Referring to the drawing, a cooled product from the pyrolysis of 1,2-dichloroethane, which is in the form of a vapor-liquid mixture, is conveyed via line 1 into a conventional quench column 2, in which the product is cooled by evaporation and contacted with a quench liquid introduced through line 6 as described hereinafter, and the product is continuously circulated in the lower section of the column by means of line 7. The gaseous reaction product is removed from the quench column in overhead line 3 and is condensed in a condenser 4 at a temperature between 40° and 50° C. and a pressure between 8 and 20 bar. The condensed product is separated into liquid and gaseous streams in vapor-liquid separator 5. The gaseous product stream is removed in line 8, and contains the major amount of the acetylene resulting from the pyrolysis process. This stream is then passed into catalytic reactor 9 which contains two beds designated 10 and 11, in succession in the direction of gas flow. Bed 10 contains a noble metal catalyst as defined hereinafter, and is maintained at a temperature between about 50° and about 200° C., preferably between about 100° and 150° C., at a pressure between about 8 and about 20 bar absolute. The gaseous stream in line 8 may be heated to the desired temperature either by means of a heater located upstream of reactor 9, or by the use of a heating jacket on the catalyst zone. Bed 11 contains a hydrochlorination catalyst as hereinafter described.

The gases exit the reactor via line 12 and this stream is then fed into the hydrogen chloride column (not shown). In this column, the hydrogen chloride is removed as overhead and passed to an oxychlorination process unit. The bottoms product of this column contains vinyl chloride and unreacted 1,2-dichloroethane and is passed downstream for further processing.

Part of the liquid product stream from vapor-liquid separator 5 is returned to the quench column as recycle in line 6, the remainder being passed via line 13 to the hydrogen chloride column.

The noble metal catalyst utilized in this process (in bed 10) is a member of the platinum group of metals, and/or a compound thereof. Preferred catalysts are the metallic form of platinum, palladium, ruthenium, and rhodium, their oxides and chlorides. Examples of noble metals and compounds which are suitable for the purposes of this invention are platinum, platinum (II) oxide, platinum (IV) oxide, hexachloroplatinic acid, platinum (II) chloride, palladium, palladium (II) oxide, ruthenium, ruthenium (IV) chloride, ruthenium (VIII) oxide, rhodium, rhodium (II) oxide, rhodium (IV) oxide, rhodium (III) chloride, and sodium hexachlororhodate (III) -dodecahydrate. Most preferred are palladium metal, palladium oxide and palladium chloride.

The noble metal catalyst is preferably supported on an inert carrier such as alumina, silica, silicates, titanium dioxide, flintstone, activated carbon, and the like. The preferred support is silica having a specific surface of 50 m$^2$/g or less. When used on a support, the catalyst bed will contain generally from about 0.05 to about 0.5 weight percent, preferably from about 0.1 to about 0.2 weight percent, of the noble metal material. However, the noble metal or compound thereof may also be used without a support.

Mercuric chloride supported on activated carbon is ordinarily used as the hydrochlorination catalyst. However, other catalysts known to promote the hydrochlorination of acetylene may be used, for instance, barium chloride, cerium chloride, mixtures of barium and mercuric chlorides, other metallic chlorides such as bismuth, antimony, iron, etc., chlorides, and optionally such compounds on other supports such as aluminum or silica gel. In general the hydrochlorination catalyst will contain from about 5 to about 20, preferably from about 8 to about 12, weight percent of the catalystically active material.

The catalytic reactor 9 may be in the form of two separate reactors or beds arranged in series, or may consist of a single reactor having two beds within it.

The process as practiced according to this invention permits the removal of undesired acetylene from 1,2-dichloroethane pyrolysis products. Surprisingly, it was discovered that when the noble metal catalyst bed is placed upstream of the hydrochlorination catalyst, the life of the downstream hydrochlorination unit or catalyst can be increased considerably when using pressures between 8 and 20 bar absolute. This result appears to be due at least in part to the consumption in the noble metal bed of hydrogen (produced in the cracking furnace) by reaction with the acetylene. Since the acetylene is converted into vinyl chloride, the desired product, thereby suppressing the formation of soot deposits and the spontaneous decomposition of acetylene into additional soot, the carbon yield of the process is improved. The purified hydrogen chloride produced by this process can be employed for the oxychlorination of ethylene.

To further illustrate the operation of the process, and the advantages achieved thereby, the following examples are presented.

EXAMPLE 1

Subsequent to the condensation stage, 1500 Nl/hour of a gaseous stream (line 8) is obtained having the following approximate composition:

75 mole % hydrogen chloride
24.7 mole % vinyl chloride
0.15 mole % 1,2-dichloroethane
0.17 mole % acetylene The stream is at a temperature of 35° C. and an overpressure of 9 bar. A liquid product (7.9 kg/hour) is also obtained (line 6), which contains only 0.005 mole % acetylene.

The total gaseous product stream is passed over a catalyst bed located in a vertically arranged reactor (diameter 55 mm, length 210 cm). Proceeding from the inlet of the reactor to the outlet, the catalyst bed consists of one liter of noble metal catalyst (bed 10) containing 0.15% by weight of palladium supported on flintstone, to a depth of 50 cm, and in the following bed 11, three liters of a hydrochlorination catalyst containing 10% by weight of mercuric chloride supported on activated carbon (type EKT 4, Lurgi Company) with a depth of approximately 155 cm. The entire reactor is surrounded by a steam jacket and the catalyst bed is maintained at a temperature of approximately 100° C. A pressure valve mounted at the exit of the reactor serves to maintain a pressure of 10 bar absolute in the catalyst bed.

Even after two months of operation, the acetylene content of the stream leaving the reactor in line 12 was on the order of less than 10 ppm by volume.

COMPARISON EXAMPLE 1

The same feed as in Example 1 was treated under the same operating conditions, with the exception that, instead of the noble metal catalyst system, the first bed 10 contained approximately 1 liter of glass Raschig rings, with no noble metal components. At the commencement the acetylene content at the outlet of the reactor was less than 10 ppm by volume. After one month of operation, this value had risen to 30 ppm by volume, and after two months of operation, to 115 ppm by volume.

EXAMPLE 2

A feed of 1000 nl/hour of a gaseous reaction product which had approximately the following composition:
- 73.5 mole % hydrogen chloride
- 26.1 mole % vinyl chloride
- 0.20 mole % 1,2-dichloroethane
- 0.20 mole % acetylene was passed through line 8, at a temperature of 40° C. and 9 bar overpressure, into a catalytic reactor 9. In the catalytic reactor the temperature was 150° C. and the overpressure was 9 bar. The first bed 10 contained one liter of noble metal catalyst comprising 0.2% by weight ruthenium supported on granular titanium dioxide (bed depth approximately 50 cm). The second bed 11 contained three liters of a hydrochlorination catalyst comprising 15% by weight of $CeCl_3 \cdot 4HgCl_2$, supported by activated carbon of the type used in Example 1. This bed had a depth of approximately 155 cm.

After two months of operation, the acetylene content of the stream leaving the reactor in line 12 was on the order of less than 10 ppm by volume.

COMPARISON EXAMPLE 2

Using the same feed as Example 2, and under the same operating conditions, except that the noble metal catalyst was replaced by one liter of glass Raschig rings, the following results were obtained.

At the commencement of the run, the acetylene content at the outlet of reactor 9 was less than 10 ppm by volume. After two weeks of operation, the acetylene content had risen to 40 ppm by volume. After one month it had risen to 70 ppm, and after two months, to 130 ppm, by volume.

The maximum tolerable acetylene concentration in the hydrogen chloride is considered to be approximately 50 ppm by volume. Thus, after two months of operation, the process according to this invention produced a stream containing one-fifth this amount, whereas after one or two months, the use of the hydrochlorination catalyst without the noble metal catalyst did not satisfy this requirement.

What is claimed is:

1. In a process for the removal of acetylene from the products of thermal pyrolysis of 1,2-dichloroethane, in which the pyrolysis products are separated into a liquid and a gaseous stream, and the gaseous stream is contacted with the hydrochlorination catalyst whereby the acetylene contained therein is converted to vinyl chloride, the improvement comprising contacting the gaseous stream, prior to contacting it with the hydrochlorination catalyst, with a catalyst comprising a noble metal or compound thereof, at a temperature of from about 50 to about 200° C., and a pressure from about 8 to about 20 bar absolute.

2. A process according to claim 1 wherein the temperature is between about 100° and about 150° C.

3. A process according to claim 1 wherein the noble metal catalyst is a member of the group consisting of platinum, palladium, ruthenium, rhodium, oxides thereof, and chlorides thereof.

4. A process according to claim 1 wherein the noble metal catalyst is a member of the group consisting of palladium, palladium oxide and palladium chloride.

5. A process according to claim 1 wherein the noble metal catalyst is supported on an inert carrier.

6. A process according to claim 1 in which the gaseous stream comprises primarily hydrogen chloride and vinyl chloride, and is contacted with the noble metal catalyst and hydrochlorination catalyst, respectively, prior to separation of hydrogen chloride from vinyl chloride.

7. A process according to claim 1 in which the gaseous stream is contacted with the noble metal catalyst, without the addition of extraneous hydrogen to said stream or catalyst.

* * * * *